United States Patent
Bui et al.

(10) Patent No.: US 10,172,689 B2
(45) Date of Patent: Jan. 8, 2019

(54) DISSOLVABLE INTRA-TOOTH SPACER

(71) Applicant: Southern Arizona Endodontics, P.C., Tucson, AZ (US)

(72) Inventors: Tung Bui, Tuscon, AZ (US); Thomas R. Kramkowski, Tuscon, AZ (US)

(73) Assignee: SOUTHERN ARIZONA ENDODONTICS, P.C., Tucson, AZ (US)

(*) Notice: Subject to any disclaimer, the term of this patent is extended or adjusted under 35 U.S.C. 154(b) by 0 days.

(21) Appl. No.: 15/279,230

(22) Filed: Sep. 28, 2016

(65) Prior Publication Data

US 2018/0085193 A1    Mar. 29, 2018

(51) Int. Cl.
  *A61C 5/02*  (2006.01)
  *C08L 29/04*  (2006.01)
  *C08L 39/06*  (2006.01)

(52) U.S. Cl.
  CPC ............ *A61C 5/02* (2013.01); *C08L 29/04* (2013.01); *C08L 39/06* (2013.01); *C08L 2205/02* (2013.01); *C08L 2205/025* (2013.01)

(58) Field of Classification Search
  CPC .... A61C 5/02; A61C 5/00; A61C 5/30; A61C 5/50; C08F 116/06; C08L 29/04; C08L 39/06
  USPC ......................................................... 433/224
  See application file for complete search history.

(56) References Cited

U.S. PATENT DOCUMENTS

| | | | |
|---|---|---|---|
| 3,913,229 A | 10/1975 | Driskell et al. | |
| 4,689,080 A * | 8/1987 | Kawahara | A61K 6/083 106/35 |
| 2001/0046518 A1* | 11/2001 | Sawhney | A61B 17/12022 424/486 |
| 2002/0198283 A1* | 12/2002 | Imai | A61K 6/0017 523/115 |

(Continued)

FOREIGN PATENT DOCUMENTS

| | | |
|---|---|---|
| DE | 9961002 | 7/2001 |
| KR | 20010077036 | 8/2001 |

(Continued)

OTHER PUBLICATIONS

Staehle et al., Comparative in vitro investigation of different methods for temporary root canal filling with aqueous suspensions of calcium hydroxide; Endod Dent Traumatol. Jun. 1997;13(3):106-12.

(Continued)

*Primary Examiner* — Nicholas Lucchesi
(74) *Attorney, Agent, or Firm* — Gavin J. Milczrek-Desai; Quarles & Brady LLP

(57) ABSTRACT

A pulp chamber dental spacer constructed of cold water soluble material, which may include portions of polyvinyl alcohol, to protect the pupal floor of a pulp chamber from a drilled hole following a root canal treatment or procedure. The spacer may be spherical or cubical in shape and that protects the pupal floor by providing a solid "space" for a practitioner to feel the end of a temporary filing such that the drill does not descend to and possibly damage the sensitive pupal floor. The dissolvable material preferably is non-linting, thereby providing for complete removal and preventing the "wicking" of contaminated salivary fluids and causing coronal damage.

6 Claims, 2 Drawing Sheets

(56) References Cited

U.S. PATENT DOCUMENTS

| | | | |
|---|---|---|---|
| 2003/0148247 A1* | 8/2003 | Sicurelli, Jr. | A61C 13/30 433/220 |
| 2004/0158194 A1* | 8/2004 | Wolff | A61C 19/063 604/66 |
| 2005/0079470 A1* | 4/2005 | Rutherford | A61K 6/033 433/226 |
| 2005/0175959 A1* | 8/2005 | Jodaikin | A61C 19/063 433/80 |
| 2007/0123603 A1* | 5/2007 | Shalaby | A61K 6/0017 523/115 |
| 2007/0281003 A1* | 12/2007 | Fuisz | A61K 9/006 424/443 |
| 2009/0215009 A1* | 8/2009 | Noishiki | A61L 27/12 433/215 |
| 2011/0104644 A1* | 5/2011 | Primus | A61K 6/0637 433/224 |
| 2012/0020899 A1* | 1/2012 | Zaidel | A61K 8/25 424/52 |
| 2012/0115982 A1 | 5/2012 | Klee et al. | |
| 2012/0270184 A1* | 10/2012 | Richard | A61K 6/0073 433/224 |
| 2012/0328708 A1 | 12/2012 | Van Der Waal et al. | |

FOREIGN PATENT DOCUMENTS

| | | |
|---|---|---|
| KR | 101445754 | 10/2014 |
| RU | 2012114035 | 10/2013 |
| RU | 2014102923 | 8/2015 |
| WO | 2011058345 A2 | 5/2011 |
| WO | 2014111255 A1 | 7/2014 |

OTHER PUBLICATIONS

Gimbel, et al, Calcium hydroxide as a temporary filling of the post space in root-filled teeth, Oral Surgery Oral Medicine Oral Pathology, vol. 94, No. 1, 2002.

Kim et al., Cytotoxicity of Root Canal Sealers Containing Calcium Hydroxide, J Kor Dent Sci. 2009;2(1):11-18.

* cited by examiner

DISSOLVABLE INTRA-TOOTH SPACER

FIELD OF THE INVENTION

This disclosure relates to pulp chamber spacers that dissolve in water and that are especially useful as a temporary wadding (instead of cotton or sponge wadding) during an endodontic procedure.

BACKGROUND OF THE INVENTION

During a root canal procedure, a hole is drilled through the enamel and into the pulp chamber of the damaged tooth for clearing out the decayed and infected tissue from the root canal(s). Usually, a sterile cotton wad or spacer is provisionally placed in the pulp chamber to support the configuration of a temporary filling. The spacer also provides a way for a practitioner to know that the bottom of a temporary filing has been reached when removal of the filling is done in preparation for the placement of a permanent crown on the tooth (i.e., a "space" is provided such that a drill or other instrument does not contact and possibly damage the pulpal floor). However, use of cotton wads may be sub-optimal for multiple reasons.

First, cotton lint fibers can be stuck between the temporary filling and tooth posing coronal leakage risks, which may increase the possibility of future infection. Additionally, cotton is insoluble in water such that fibers will remain intact if caught during irrigation or otherwise left within a tooth and harbor bacterial growth if not completely removed.

Therefore, a need exists for a novel absorbent spacer for use below a temporary filling that does not pose a leakage risk and that can more effectively be removed.

SUMMARY OF THE INVENTION

Embodiments herein relate to a pulp chamber spacer composed of a solid, deformable wadding material that is dissolvable in water. Further embodiments are directed to methods of use for the pulp chamber spacers disclosed herein.

In preferred embodiments, non-linting material is used to decrease the possibility of coronal leakage and the associated post-temporary filling or permanent crown infections within the endodontically treated tooth.

In one embodiment, the compositions include a polyvinyl alcohol dipolymer that is soluble in cool water and therefore does not "lint" or leave behind portions within the tooth. To achieve cool-water solubility, the polyvinyl alcohol (PVOH) polymer may preferably be 70-80% hydrolyzed.

In some embodiments, the polymer may be modified by 5-10% cyanoethylation, 1-20% acetalization, 1% urethanization, or synthesized as a 50:50 mixture of polyvinyl alcohol and polyvinyl pyrrolidone, for example.

In still other embodiments, one or more medicaments may be added to the spacer, such as calcium hydroxide and/or chlorhexidine to provide anti-microbial properties.

BRIEF DESCRIPTION OF THE DRAWINGS

Some embodiments of the disclosed invention are illustrated in the following figures.

DETAILED DESCRIPTION OF THE INVENTION

Fully hydrolyzed PVOH, where virtually all the acetate groups have been converted to alcohol groups (e.g., 98% or greater degree of hydrolysis), is a strongly hydrogen-bonded, highly crystalline polymer which dissolves only in hot water—e.g., rapid dissolution at temperatures of about 150° F. and greater.

If a sufficient number of acetate groups are allowed to remain after the hydrolysis of polyvinyl acetate, the PVOH polymer then being known as partially hydrolyzed, it is more weakly hydrogen-bonded and less crystalline and is soluble in cold water—e.g., rapid dissolution at temperatures of about 50° F. and greater.

The average cold water inlet in a U.S. municipality can range from less than 50° F. (colder climates) to over 80° F. (warmer climates). By extension, many dental irrigation water lines provide water within this temperature range (unless heated). Thus, as used herein, "cold water dissolution" is defined as complete or near complete dissolution that occurs between about 50° F. and about 80° F., where "about" is further defined as plus or minus 10%.

The term PVOH copolymer is generally used to describe polymers that are derived by the hydrolysis of a copolymer of a vinyl ester, typically vinyl acetate, and another monomer. PVOH copolymers can be tailored to desired film characteristics by varying the kind and quantity of copolymerized monomers. Examples of copolymerizations are those of vinyl acetate with a carboxylic acid or with an ester of a carboxylic acid. Again, if the hydrolysis of acetate groups in these copolymers is only partial, then the resulting polymer could also be described as a PVOH terpolymer—having vinyl acetate, vinyl alcohol, and carboxylic acid groups—although it is commonly referred to as a copolymer.

In one type of embodiment, the spacer preferably is essentially free of crosslinking agents, or completely free of crosslinking agents, for the water-soluble polymer. In another type of embodiment, only a small amount of a weak crosslinking agent will be used.

For PVOH as the water-soluble polymer, crosslinking agents can be selected from any chemical agent that can form chemical bonds with the hydroxyl groups of PVOH. Such crosslinking agents include, for example, monoaldehydes (e.g., formaldehyde and hydroxyacetaldehyde), dialdehydes (e.g., glyoxal, glutaraldehyde and succinic dialdehyde), aldehyde-containing resins (e.g., trimethylol melamine), dicarboxylic acids (e.g., maleic, oxalic, malonic and succinic acids), citric acid, glycidyl and other difunctional methacrylates, N-lactam carboxylates, dithiols (e.g., m-benzodithiol), boric acid and borates, ammonium zirconium carbonate, inorganic polyions (e.g., molybdate and tungstate), cupric salts and other Group 1B salts, and polyamide-epichlorohydrin resin (polyazetidine prepolymer).

Figure 1:
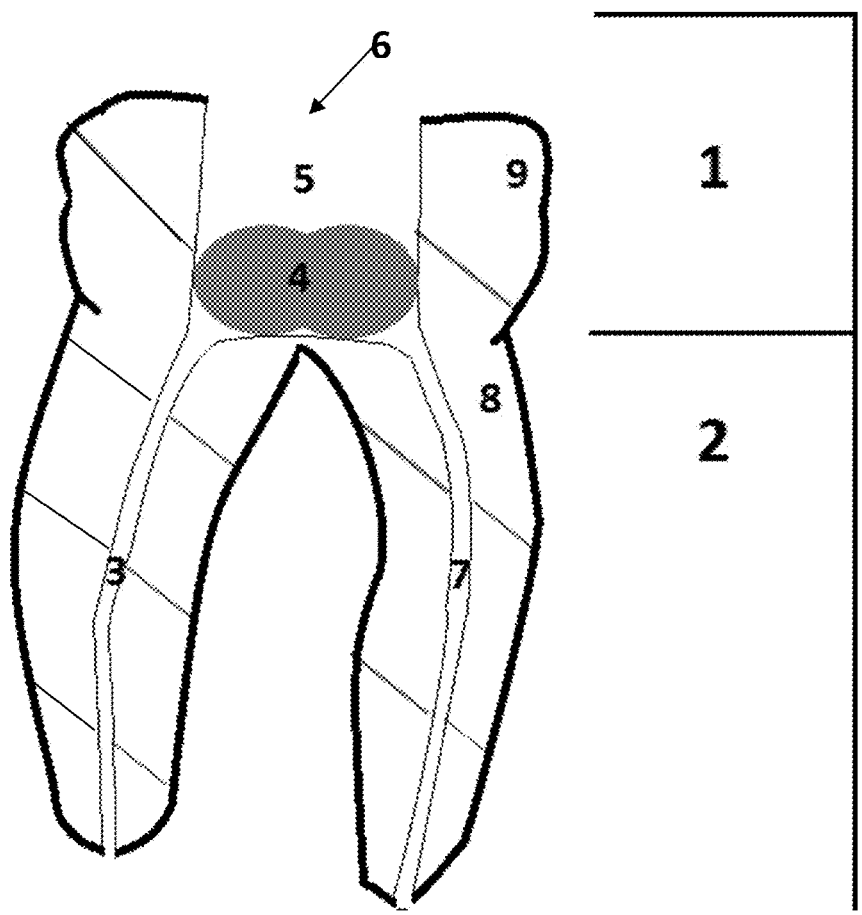
FIG. 1 illustrates a cross-sectional view of a tooth in which one example of a pulp chamber spacer has been positioned directly below the opening for a temporary filling.

FIG. 1 depicts a cross-sectional view of a dissolvable pulp chamber spacer (the "spacer") according to the various embodiments described herein. In its preferred embodiment, the pulp chamber spacer 4 is spherical in shape and is composed of a "foam-like" absorbent material that is soluble in water at temperatures at or below about 80° F. ("cold water"). The absorbent material may consist of 70-80% hydrolyzed polyvinyl alcohol polymers, 5-10% cyanoethylated polyvinyl alcohol polymers, 1-20% acetalized polyvinyl alcohol polymers, 1% urethanized polyvinyl alcohol polymers, 50:50 polyvinyl alcohol and polyvinyl pyrrolidone dipolymers or other similar materials which may produce a cold water soluble spacer composed, preferably, of "non-linting" material such that none of the spacer is left in the pulp chamber upon irrigation of same with water.

Moreover, one or more medicaments may be added to the spacer. For example, calcium hydroxide and/or chlorhexidine may be added to provide anti-microbial properties.

The spacer or wad may be positioned at the bottom of the pulp chamber 5, in the place of the pulp chamber, such that is substantially conforms to and at least partially fills the pulp chamber (which is de-pulped prior to positioning of the spacer). The spacer 4 may occupy the hole 6 that is accessed through the crown 1 and atop the root 2 regions. In other words, the spacer 4 is positioned through the hole in the enamel 9, next to the dentin 8 of the perimeter of the hole, and atop root canals 3, 7.

The spacer 4 separates the temporary filling (not shown) from the root canals 3, 7 and provides ease of temporary filling removal in the future (i.e., improved "feel" of the solid spacer where the filling ends versus cotton, such that there is less drilling towards the root canals, which reduces the risk of damage to the pupal floor of the tooth).

Figure 2:
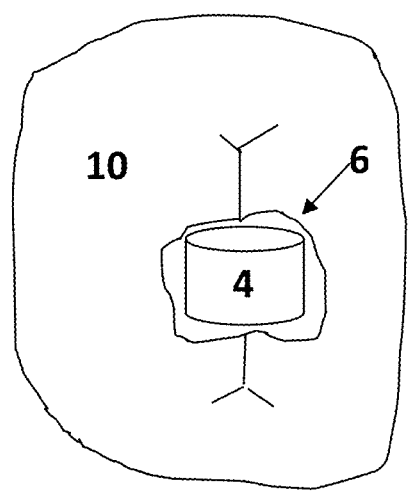
FIG. 2 is an illustration of a top view of a pulp chamber spacer applied to the pulp chamber hole post-tissue removal according to the various embodiments described herein.

FIG. 2 depicts a top view of the tooth with applied spacer 4 without a temporary filling. The spacer 4 is placed within typically 1-4 millimeters of the crown region 10. The spacer is not necessarily to scale, as ordinarily it would be slightly larger than the hole 6 but deformable so as to go through the hole and substantially fill the bottom and sides of the pulp chamber up to a certain number of millimeter of the crown.

Figure 3:
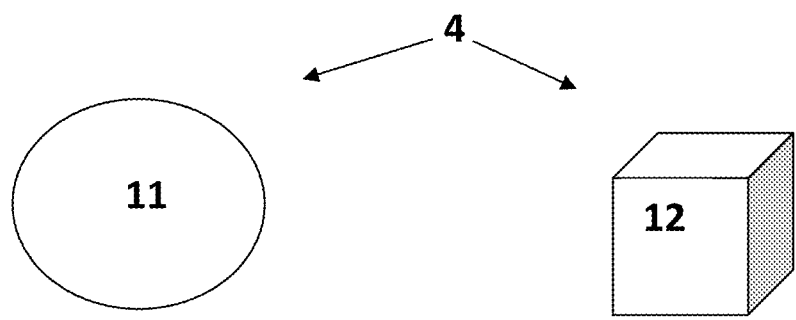
FIG. 3 is an illustration of a perspective view of a third embodiment of a pulp chamber spacer.

FIG. 3 depicts the spherical or cube shape of two other embodiments of the spacer 4. In this example, the sphere spacer 11 and cube spacer 12 are formed into a single-piece of material.

From the above, a method for prevention of wicking of saliva inside a tooth that has undergone a root canal is apparent, including placing a solid, deformable material in a de-pulped tooth interior atop a root chamber, with the material being dissolvable in cold water. A temporary filling can then be placed. When the temporary filling is removed, the practitioner rinses the dissolvable solid material with water to thereby dissolve it. The permanent crown can then be placed.

Although the disclosed invention has been described herein with respect to preferred embodiments, other equivalent examples may perform like functions and/or obtain similar results. All such similar or sufficient embodiments are intended to be covered by the claims in this application. For example, an injectable gel or paste composition that forms a deformable solid that is cold water soluble may be used.

What is claimed is:

1. A method of preparing a de-pulped pulp chamber of a tooth that has undergone a root canal procedure for placement of a permanent crown or filling, comprising the steps of:

positioning a solid, deformable and water-dissolvable spacer at the bottom of the pulp chamber such that said spacer substantially conforms to and at least partially fills the pulp chamber and is positioned atop a root region; and rinsing the solid, deformable, dissolvable spacer with water to thereby dissolve said spacer prior to placement of the permanent crown or filling, wherein said spacer is larger than a hole in said tooth through which it is positioned in the pulp chamber and said spacer is deformed so as to go through the hole during positioning.

2. The method of claim 1, wherein said spacer is a non-linting material and comprises a polymer composed of about 70-80% hydrolyzed polyvinyl alcohol polymers.

3. The method of claim 1, wherein said spacer includes one or more of 5-10% cyanoethylated polyvinyl alcohol polymers, 1-20% acetalized polyvinyl alcohol polymers, 1% urethanized polyvinyl alcohol polymers, 50:50 polyvinyl alcohol and polyvinyl pyrrolidone dipolymers.

4. The method of claim 1, wherein said spacer is a single-piece of material and is spherical in shape.

5. The method of claim 1, wherein said spacer is a single-piece of material and is cubical in shape.

6. The method of claim 1, wherein the spacer is positioned such that said spacer is within 1-4 millimeters of a crown region of said tooth.

* * * * *